| United States Patent [19]
Tamura et al.

[11] 4,254,225
[45] Mar. 3, 1981

[54] NOVEL NEUTRAL GLUCOAMYLASE AND METHOD FOR ITS PRODUCTION

[75] Inventors: Masaki Tamura, Kamakura; Mizuho Shimizu, Hino; Minoru Tago, Tokyo, all of Japan

[73] Assignee: CPC International Inc., Englewood Cliffs, N.J.

[21] Appl. No.: 55,717

[22] Filed: Jul. 9, 1979

[30] Foreign Application Priority Data

Jul. 20, 1978 [JP] Japan ................................ 53-87812

[51] Int. Cl.³ .......................... C12P 19/20; C12N 9/34

[52] U.S. Cl. ........................................ 435/96; 435/205; 435/911

[58] Field of Search .......................... 435/96, 205, 911

[56] References Cited

U.S. PATENT DOCUMENTS 4,017,363  4/1977  McMullen ............................... 435/96

Primary Examiner—Lionel M. Shapiro

[57] ABSTRACT

Process for the production of a glucoamylase having a pH optimum at about 6.0 to 6.5 by a strain of Stachybotrys and the glucoamylase produced thereby.

11 Claims, 4 Drawing Figures

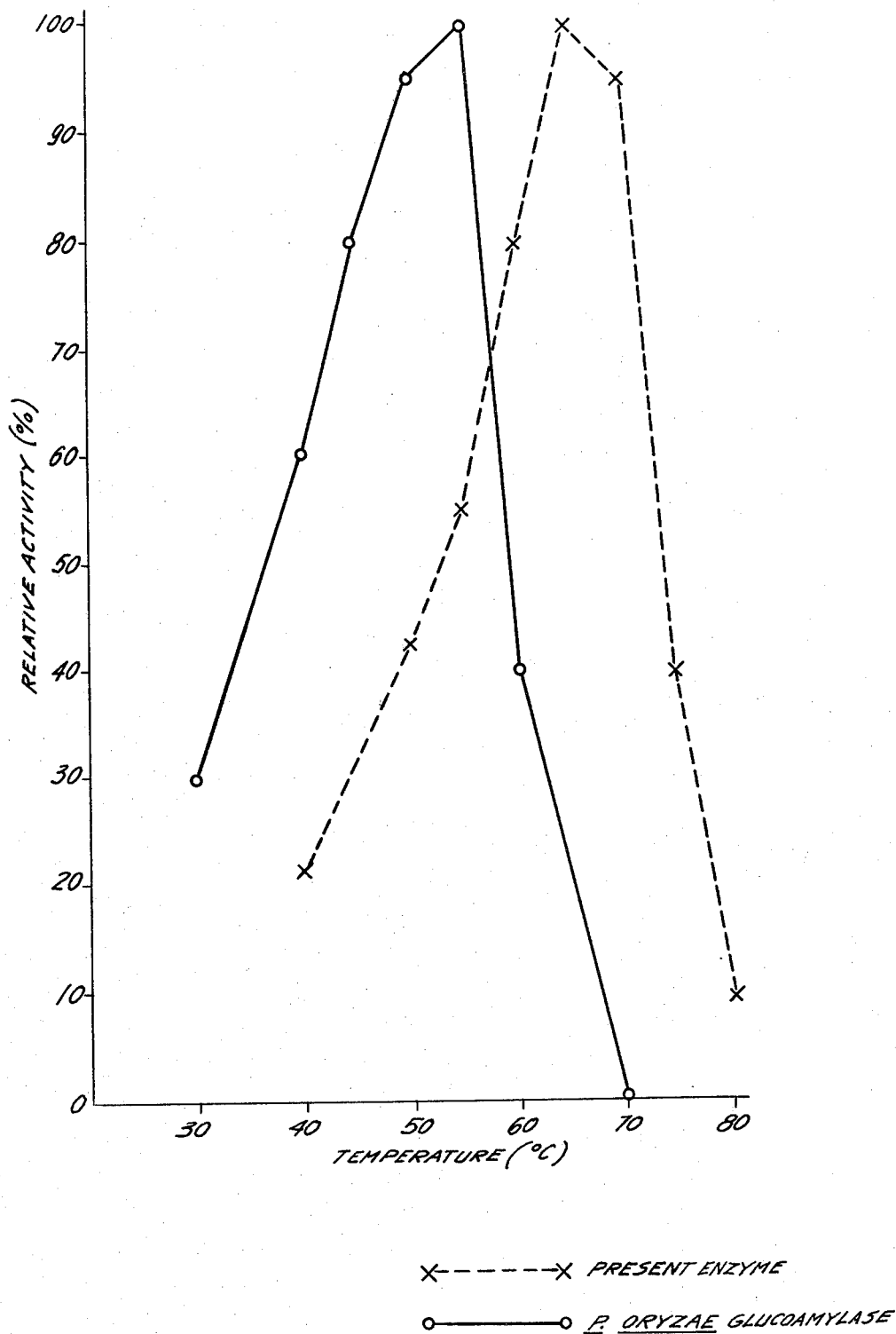

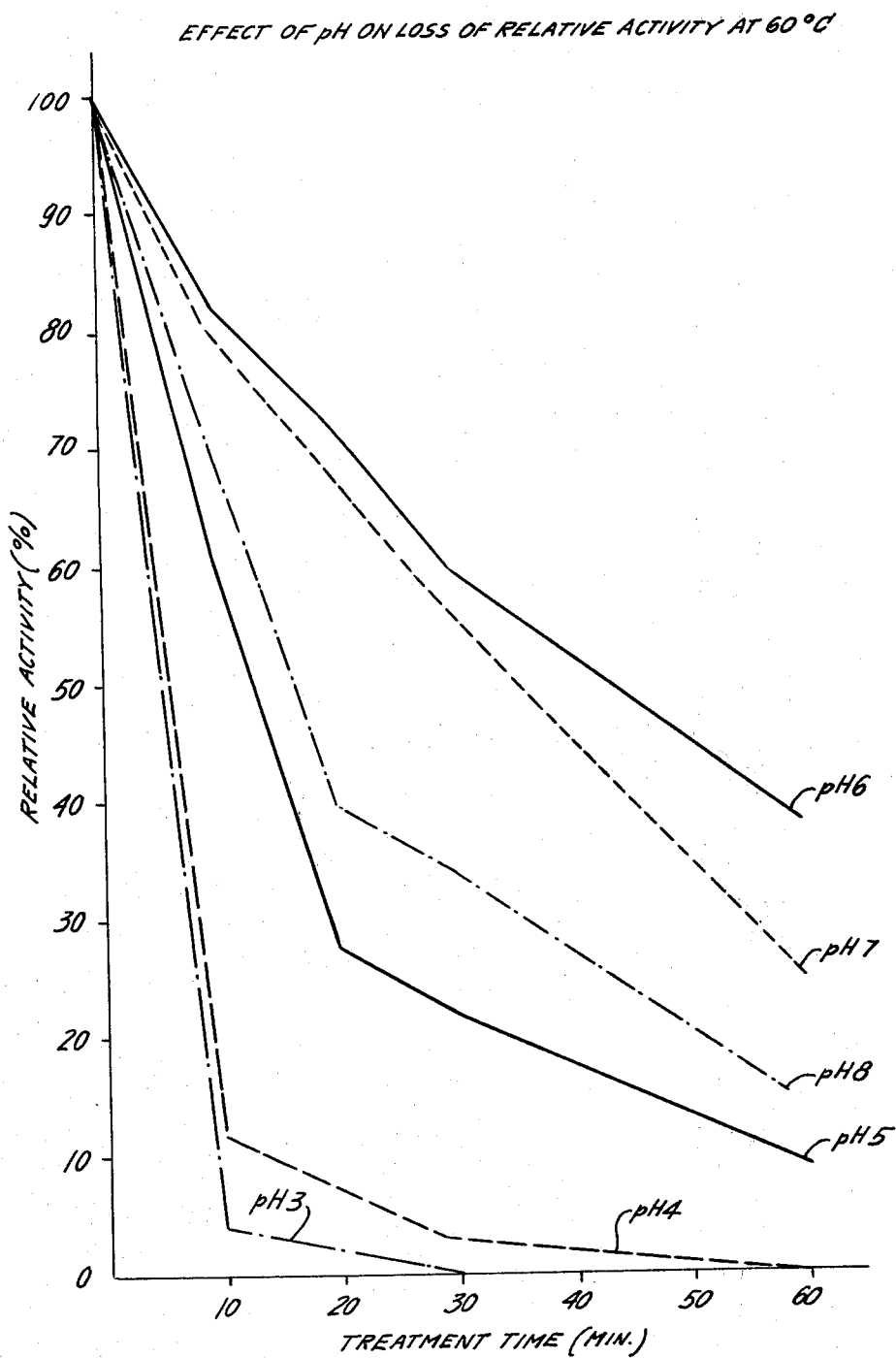

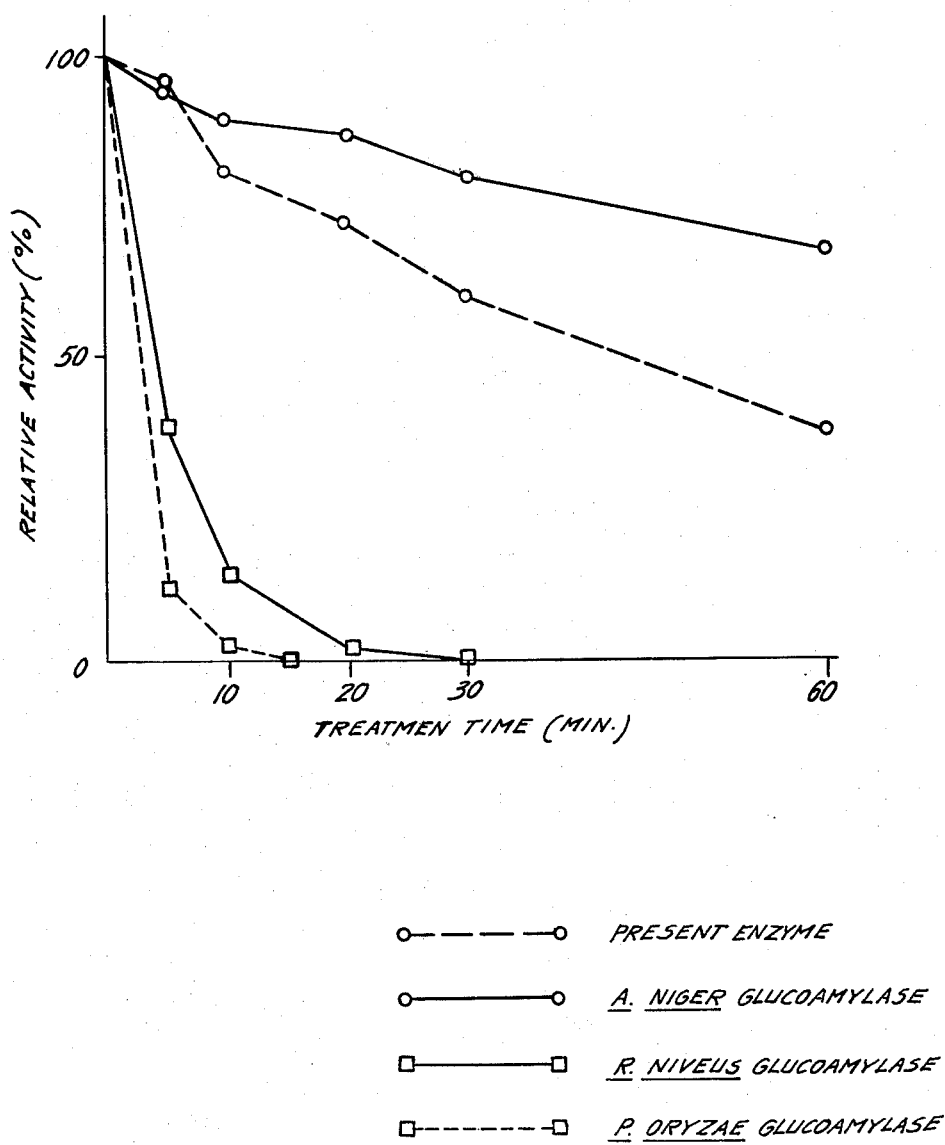

NOVEL NEUTRAL GLUCOAMYLASE AND METHOD FOR ITS PRODUCTION

BACKGROUND OF THE INVENTION

At present, when producing dextrose industrially from starch, the principal glucoamylases employed for the saccharification process are those produced by microorganisms belonging to the genera Rhizopus and Aspergillus. The conditions under which these glucoamylases are employed are pH 5.0 and 55° C. for the enzyme of the Rhizopus microorganism, and pH 4.5 and 60° C. for the Aspergillus microorganism's enzyme. In addition, maximum dextrose content of the hydrozylate is about 96% (dry solids basis) when these glucoamylases react with enzyme liquefied starch at a 30% concentration. One reason that the dextrose yield does not reach 100% is that isomaltose accumulates due to a reverse reaction by these glucoamylases. However, there was recently published a report (U.S. Pat. No. 3,897,305) that the reverse reaction of glucoamylses is extremely small in the vicinity of neutrality and that the dextrose yield can thus be elevated to about 98% by carrying out the reaction at about a neutral pH with the joint use of pullulanase. The pullulanase acts to debranch the starch and increases the rate of glucoamylase action under these nearly neutral conditions. As far as neutral glucoamylases are concerned, only one has been reported to date, that being the glucoamylase produced by the rice blast-causing fungus (*Piricularia oryzae;* Kazuo Matsuda, et al: Amylase Symposium, Vol. 9, 1974), but this glucoamylase possesses low thermostability and so cannot be employed under industrial conditions.

SUMMARY OF THE INVENTION

It is therefore a primary object of the present invention to provide a glucoamylase that is active at nearly neutral pH.

It is another object of the invention to provide a glucoamylase that possesses enough thermostability so that it can be employed under industrial reaction conditions.

It is yet another object of the invention to provide a glucoamylase that reacts with a starch hydrolyzate to give high yields of dextrose.

A microbial strain has been discovered which produces a new glucoamylase having optimum activity at a pH of 6.0 to 6.5 and good thermostability. The new glucoamylase is capable of converting a 30% by weight solution of a 10 D.E. (dextrose equivalent) liquefied starch to a product containing at least about 96% dextrose when reacted with the starch hydrolyzate at pH 6.0 to 6.5 at 55° C. This invention includes the method for the production of this glucoamylase wherein the microorganism of the genus Stachybotrys, which produces the glucoamylase, is cultured in a medium and the enzyme is recovered from the culture broth.

BRIEF DESCRIPTION OF THE DRAWINGS

FIG. 2 shows the relationship between the temperature and the enzyme activity in the cases of the present enzyme and the glucoamylase from *P. oryzae*.

FIG. 3 presents the inactivation curves for the enzyme of this invention when it is treated at various pH levels.

FIG. 4 provides a comparison of the present enzyme and the conventional glucoamylases produced by the *R. niveus, A. niger* and *P. oryzae* microorganisms in terms of their relative thermostabilities.

DETAILED DESCRIPTION OF THE INVENTION

Figure 1:
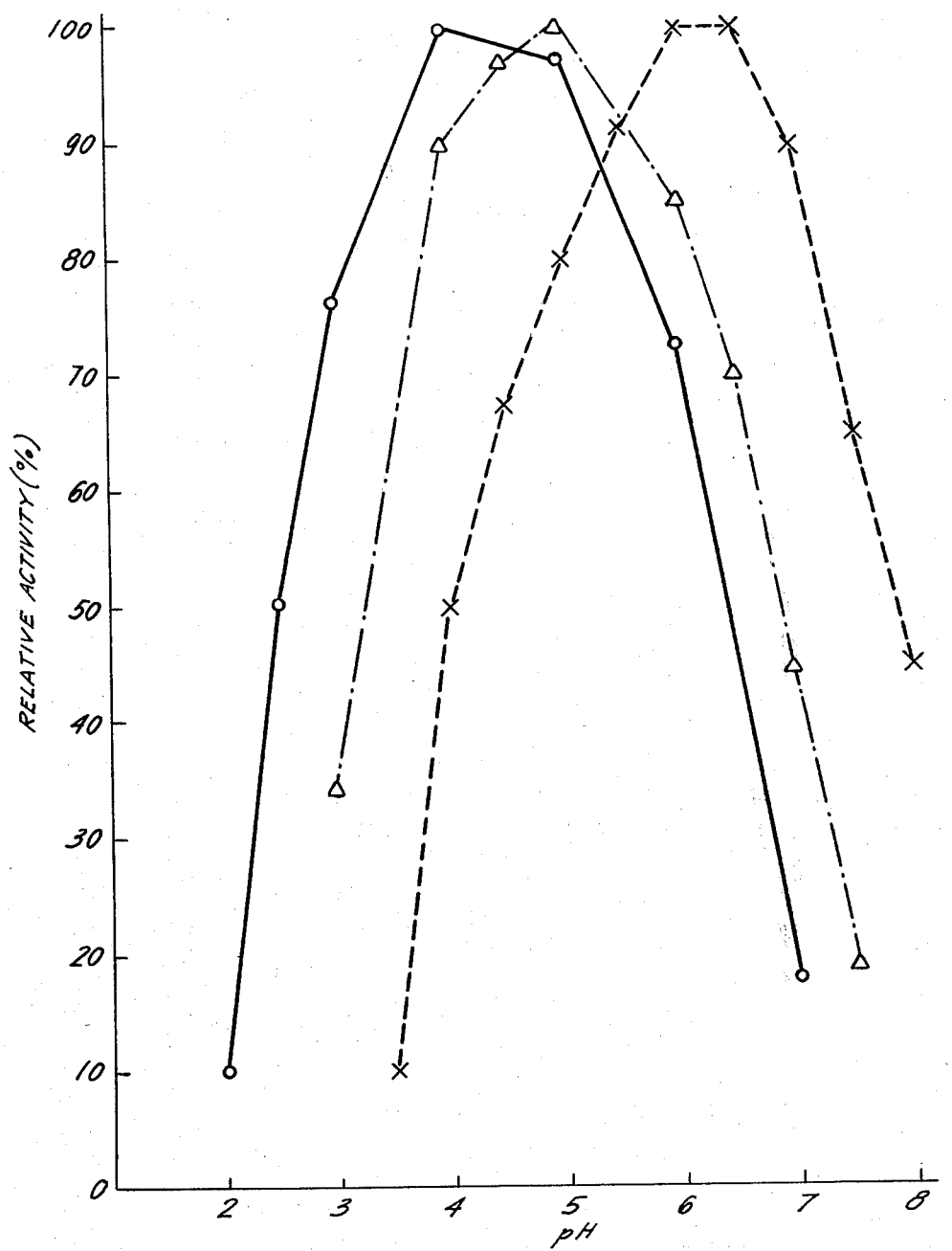
FIG. 1 shows the relationship between the pH and the enzyme activity in the cases of the enzyme of the present invention and the conventional glucoamylases produced by *R. niveus* and *A. niger* microorganisms.

The properties of the novel neutral glucoamylase of the present invention are presented in detail, and their properties are contrasted with those of the previously-known glucoamylases.

The term "D.E." is an abbreviation for "dextrose equivalent," and these terms are used interchangeably to refer to the reducing sugar content of a material calculated as dextrose and expressed as percent of total solids.

The term "starch hydrolyzate" is used in a general way to refer to a syrup or dry product that is made by the partial hydrolysis of starch. Such a product may be made by acid or enzymic hydrolysis.

The term "liquefied starch" is used to refer to a low D.E. (D.E. from about 2 to about 20) starch hydrolyzate.

1. Activity and Substrate Specificity

The present enzyme is able to hydrolyze such carbohydrate compounds as starch, soluble starch, amylose, amylopectin and glycogen, and to produce dextrose from them. The yield of dextrose from each of these substrates is 100% when the substrate concentration is 1%. The mutarotation of the produced dextrose is positive. This enzyme is thus a glucoamylase. The reaction velocity of this enzyme was compared to the rates shown by the glucoamylases produced by microorganisms belonging to Rhizopus and Aspergillus in relation to various substrates. The results are presented in Table I. As can be seen from this table, the activity of the present enzyme is notably higher than the activities of the other two glucoamylases especially in relation to the hydrolysis of pullulan.

TABLE I

| | SUBSTRATE SPECIFICITY | | |
|---|---|---|---|
| | Reaction Rate[a] | | |
| Substrate | Present Enzyme | Aspergillus niger Glucoamylase[b] | Rhizopus niveus Glucoamylase[c] |
| Dextrin (D.E. 10) | 100 | 100 | 100 |
| Amylpectin | 104 | 113 | 91 |
| Soluble Starch | 122 | 95 | 112 |
| Pullulan | 9 | 2 | 2 |
| Glycogen | 102 | 100 | 91 |
| Maltotriose | 6 | 12 | 8 |
| Maltohexaose | 91 | 100 | 146 |
| Panose | 44 | 47 | 48 |
| Maltose | 14 | 26 | 19 |

[a]The enzymatic activities of each glucoamylase were determined with the substrates present at a 1% concentration; each enzyme's activity in relation to dextrin was assigned the value 100, and the activities on the other substrates are presented as relative values
[b]Available from Enzyme Development Corporation, 2 Penn Plaza, New York, N.Y.
[c]Sumyzyme available from Sumitomo Shoji Kaisha, Ltd., 1, Kanda Mitoshiro-Cho, Chiyoda-ku, Tokyo, Japan.

2. Optimum pH and Stable pH Range

The relationship between the enzymatic activity (relative value) of the present enzyme and the reaction pH were investigated and then compared with the corresponding relationships for the conventionally-known glucoamylases produced by the Rhizopus and Aspergillus microorganisms. The results are presented in FIG. 1. As shown in the figure, the optimum pH of this enzyme at 60° C. is 6.0 to B 6.5, considerably higher than the pH optima of the other enzymes. In addition, this enzyme shows its best stability in the vicinity of pH 6.0, but no inactivation of this glucoamylase is seen even when it is left sitting for 24 hours at room temperature, over a pH range of 4 to 11.

3. Determination of Potency

A 0.5-ml aliquot of a suitably diluted enzyme solution was added to 0.5 ml of a 2% solution of a spray-dried maltodextrin (D.E. about 10) in 0.1 M acetate buffer solution (pH 6.0) and this was incubated at 60° C. for precisely 10 minutes. The enzyme reaction was then stopped by heating the mixture for 5 minutes in a boiling water bath. The amount of dextrose produced was determined by the glucose oxidase method. The amount of enzyme producing 1 micromole of dextrose per minute was defined as 1 unit.

4. Optimum Reaction Temperature Range

The effect of temperature on the relative enzymatic activity of the present enzyme at pH 6.0 was compared with the relative activity for the known glucoamylase from the rice blast fungus, *Piricularia oryzae*. This comparison is shown in FIG. 2. It is evident that the optimum temperature for the reaction of the present enzyme under these conditions is 65° C., about 10° C. higher than that of the enzyme from *Piricularia oryzae*.

5. Inactivation Due to pH and Temperature Conditions

FIG. 3 presents inactivation curves of the relative enzymatic activity of the present enzyme when it was treated for 60 minutes at 60° C. over a pH range of 3 to 8. As is clear from the figure, this enzyme is most stable at pH 6, and it is completely inactivated by this treatment for 30 minutes at pH 3 and for 1 hour at pH 4. In addition, FIG. 4 shows a comparison of the thermostability of the present enzyme and the glucoamylases from the Rhizopus, Aspergillus and Piricularia microorganisms. Namely, FIG. 4 presents the inactivation curves obtained for these enzymes when they were treated at 60° C. while being held at their respective optimum pH's for stability. It can be seen that the thermostability of the present enzyme is inferior to that of the glycoamylase of Aspergillus origin, but is superior to the thermostability shown by the glucoamylases from the Rhizopus and the Piricularia microorganisms.

6. Inhibition, Activation and Stabilization

This enzyme does not require any special activating or stabilizing agents. However, the same as in the case of most of the other glucoamylases, this enzyme is inhibited by mercuric chloride, potassium manganate, ferrous chloride, other metal salts and tris.

7. Purification Procedure

The present enzyme can be purified by means of a combination of any of the ordinary purification methods such as ammonium sulfate fractionation, organic solvent fractionation, starch adsorption, and various chromatographies. An illustrative example of such a purification procedure is presented next.

The cells and other insoluble material are eliminated from the cultured material and then the culture fluid is frozen overnight at −20° C. This is then melted at room temperature and the insoluble matter is removed by centrifugation. Next, two volumes of cold isopropanol is added to this and it is left standing for one night at 4° C. The enzyme precipitates and the supernatant is removed by decantation. The precipitate is then dissolved in a 0.05 M tris-HCl buffer solution (pH 7.5) containing 1 mM EDTA, and the dissolved material is next dialyzed for one night at 4° C. against the same buffer. DEAE-cellulose which has been equilibrated with the same buffer solution is next added to this dialyzed enzyme solution so that the enzyme is adsorbed thereto. After washing this DEAE-cellulose with the same buffer, enzyme is eluted from the resin with a preparation of the same buffer containing 0.3 M NaCl. The enzyme is then precipitated by the addition of two volumes of cold isopropanol to the eluate, and this precipitated material is recovered by centrifugation. The precipitate is dissolved in the 0.05 M tris-HCl buffer solution (pH 7.5) containing 1 mM EDTA, followed by overnight dialysis against the same buffer. The dialyzed enzyme solution is next applied to a DEAE-cellulose column which has been equilibrated with the same 0.05 M tris-HCl buffer (pH 7.5) containing 1 mM EDTA. The enzyme is then eluted from this column by passing through it a linear concentration gradient of the same buffer containing NaCl up to 0.5. M. The eluted fractions which contain the enzyme are pooled and the enzyme is concentrated by means of the isopropanol precipitation technique. This concentrated enzyme is then applied to a column of Sephadex G-150 which has been equilibrated with a 0.05 M tris-HCl buffer (pH 7.0) containing 1 mM EDTA, and elution is carried out with the same buffer solution. When this procedure was followed, the purified enzyme which was obtained showed a single band in disc electrophoresis.

8. Molecular Weight

The molecular weight of the present enzyme was investigated using a Sephadex G-150 column in accordance with the procedure of Andrews, P., Biochem. J. 96, 595 (1965). The results indicated that this enzyme's molecular weight is about 50,000.

Next, the points of difference between the present enzyme and the conventionally-known glucoamylases will be presented, and an explanation will be made of the reasons that this enzyme is to be considered a new enzyme having its optimum pH in the vicinity of neutrality.

Regarding the optimum pH of enzymes, it can be seen from the data presented in FIG. 1 and Table II that the only glucoamylases which have their optimum pH's near the neutral zone are the present enzyme and the glucoamylase produced by the rice blast microorganism, *Piricularia oryzae*. However, as is clear from FIG. 2 and Table II, the present enzyme and the rice blast glucoamylase have optimum reaction temperatures which are extremely different. In addition, the curves presented in FIG. 4 indicate that the thermostability of the present enzyme is vastly superior to that of the rice blast glucoamylase. Moreover, Table II shows that the molecular weight of the present enzyme is much smaller than the molecular weight of the other known glucoamylases

TABLE II

COMPARISON OF VARIOUS GLUCOAMYLASES IN TERMS OF OPTIMUM pH, OPTIMUM TEMPERATURE AND MOLECULAR WEIGHT

| Glucoamylase | Optimum pH[a] | Optimum Temp. °C.[a] | Molecular Weight[a] |
|---|---|---|---|
| Present Enzyme (*Stachybotrys subsimplex*) | 6.0–6.5* | 65* | 50,000* |
| *Rhizopus* sp. (Sumyzyme) | 5.0* | 60* | 70,000[b] |
| *Aspergillus niger* | 4.5* | 70* | 97,000[c] |
| *Endomyces* sp.[d] | 5.0 | — | 64,000 |
| *Endomyces fibuligera*[e] | 5.5 | 60 | — |
| *Trichoderma viride*[f] | 5.0 | 60 | 75,000 |
| *Cephalosporium charticola*[g] | 5.4 | 60 | 69,000 |
| *Piricularia oryzae*[h] (rice blast org.) | 6.5 | 55 | 94,000 |

[a] All values except those marked with an asterisk (*) were taken from the references.
[b] Hiromi, et al: Biochem. Biophys. Acta 302, 362 (1973).
[c] J. H. Pazur, et al: J. Biol. Chem. 237, 1002 (1962).
[d] Hattori, et al: Agr. Biol. Chem. 25, 895 (1961).
[e] Harada, et al: J. Ferment. Tech. 53, 559 (1975).
[f] Okada: J. Jap. Soc. Starch Sci. 21, 283 (1974).
[g] H. Urbanek, et al: Appl. Micro. 30, 163 (1975).
[h] Matsuda, et al: Amylase Symposium 9, 105 (1974).

On the basis of the above facts, it can be concluded that the glucoamylase produced by the method of the present invention is a new neutral glucoamylase which has been totally unknown to date.

An explanation will now be made of the method for the production of the present enzyme.

As a desirable example of the glucoamylase-producing microorganism to be used in the present invention, there is strain G30-1140, which was isloated from the soil by the present inventors. The identification of this strain will be presented first.

The morphological properties of the present strain were determined in accordance with the methods described by the researchers listed below:

Gilman, J. C. A MANUAL OF SOIL FUNGI. The Iowa State University press, Ames. 1971.

Clements, F. E. and Shear, C. L. THE GENERA OF FUNGI. Hafner, N.Y. 1964.

Barnett, H. L. ILLUSTRATED GENERA OF IMPERFECT FUNGI. 2nd ed. Burgess, Minneapolis. 1968.

Bisby, G. R. Trans. Br. Mycol. Soc. 26, 133–43 (1943).

Ainsworth, G. C. DICTIONARY OF THE FUNGI. 6th ed. Commonwealth Mycological Institute, Kew, Surrey. 1971.

9. Morphological Properties of Strain G30-1140

The present strain was cultured on five kinds of media in Petri dishes. The following sections present the morphological characteristics which were observed for isolated colonies.

(a) Czapek Agar Medium

When incubated at 30° C. for 10 days, the colonies are thin and round, with a diameter of 4 to 5 cm. The vegetative hyphal are hyalin and show poor growth with black conidial clusters scattered like powder over the surface of the colonies. The undersides of the colonies are a brown color, and a tan pigment is secreted into the medium.

The vegetative hyphal consist of branched fibers which rarely possess any septa; the conidial structure is uniformly supported by the fibers. The conidiophores which have septa protrude from this at right angles. The length of the conidiophores is usually from 40 to 60μ, but sometimes they attain more than 100μ. The diameter of these is about 3 to 6μ, and although there are cases when the basal area of these is smooth, most of their surface is verrucose, being covered with fine granular projections. These conidiophores are hyalin, and most are not branched.

On the apex of the conidiophores, hyalin phialides form whorls of 3 to 8 units. The shape of the phialides is ovoid or flask-like; they are 8 to 15μ in length and have a diameter of 2 to 6μ; their surface is smooth. The conidia are formed at the apex of the phialides and are oval shapes of 3 to 5μ×5 to 10μ, and have a smooth surface. These are hyalin at the time of formation, but become blackish green as they mature.

The surface of the conidia is covered with a large amount of viscous material. For this reason, the conidia stick together and form large conidial clusters at the apex of the conidiophores. The viscous material is transparent at the time that it is formed, but then gradually becomes black.

(b) Modified Czapek Agar Medium

| | Percent |
|---|---|
| Soluble Starch | 1.0 |
| Corn Steep Liquor (dry solids basis) | 0.1 |
| NaNO$_3$ | 0.2 |
| K$_2$HPO$_4$ | 0.1 |
| KCl | 0.05 |
| MgSO$_4$ . 7H$_2$O | 0.05 |
| FeSO$_4$ . 7H$_2$O | 0.001 |
| Agar | 2.0 |
| pH to 7.0 with NaOH | |

The growth of colonies on this medium is a bit slower than on the previously described Czapek medium, reaching about 3 cm when incubated for 10 days at 30° C.

The colonies are circular and thin, and their surfaces have radiating from their centers a black viscous material which is in the form of oil-like drops having diameters reaching 1 to 3 mm. These arise from the gathering together of clusters of conidia which are enclosed in the viscous material and then form oil-drop-like bodies. The undersides of the colonies show a darker brown color than is seen with the previous Czapek medium, and a small amount of brown pigment is secreted into the medium.

(c) Potato-Dextrose Agar Medium

The growth of colonies on this medium is a bit slower than on the previously-described Czapek medium, reaching 3 to 4 cm when incubated for 10 days at 30° C. These colonies are also circular, but they have a somewhat greater thickness than the colonies on the Czapek medium. The growth of the vegetative cells is good, developing in a radiating pattern. The surfaces of the colonies are black with a slightly green luster, and are rich in hyphae, conidial clusters and so on. After 14 days of incubation, the surfaces of the old colonies have radiating formations of synnemata standing about 1 to 3 mm erect. The undersides of these colonies show a blackish-brown color, and a large amount of brown pigment is secreted into the medium.

(d) Special Agar Medium

|  | Percent |
| --- | --- |
| Soluble Starch | 1.0 |
| Corn Steep Liquor (dry solids basis) | 0.2 |
| Cottonseed Oil Dregs | 0.1 |
| Yeast Extract | 0.1 |
| $K_2HPO_4$ | 0.1 |
| $MgSO_4 \cdot 7H_2O$ | 0.05 |
| Agar | 2.0 |
| pH to 7.0 with NaOH | |

The colonies on this medium after 10 days of incubation at 30° C. have diameters of 5 to 6 cm, and are round and thin. The vegetative hyphae show good growth and have a black luster. The growth of conidia is worse than on the above-mentioned media. The undersides of the colonies are tan in color, and a tan pigment is released into the medium.

(e) Davis's Yeast Salt Agar Medium

The colonies on this medium after 10 days of incubation at 30° C. have diameters of 2 to 3 cm and are more oval than round in shape. The hyphae are tan with a touch of white and form somewhat thick colonies which are velvety. The undersides of the colonies are tan in color, but absolutely no pigment is secreted into the medium.

10. Physiological Properties of Strain G30-1140

(a) Growth Temperature

This strain is capable of growth over a temperature range of 10° to 37° C., but its optimum growth temperature is in the vicinity of 30° C.

(b) Growth pH

This strain is capable of growth over a pH range of 3 to 10, but its optimum growth pH is in the vicinity of pH 7.

(c) Carbon Source

This strain is capable of using such carbon sources as dextrose, fructose, galactose, mannose, saccharose, maltose and starch in order to support its growth.

On the basis of the above microbiological findings, strain G30-1140 was identified as *Gliobotrys alboviridis* after consulting the GENERA OF FUNGI and A MANUAL OF SOIL FUNGI. However, according to the DICTIONARY OF THE FUNGI and G. R. Bisby (Trans. Br. Mycol. Soc. 26, 133-43 (1943)), this organism is the same as *Stachybotrys subsimplex*, and for this reason strain G30-1140 was identified as *Stachybotrys subsimplex*.

Strain G30-1140 has conidiophores which stand erect from its vegetative hyphae, branching is almost nonexistent, and they have septa. There are occasions when the basal part is smooth, but the apex is covered with projections. At the apex, a level of phialides form a whorl of 3 to 8 units. Conidia having smooth oblong surfaces divide from these phialides, and they are enclosed in a richly viscous substance. These properties agree well with those described for *Stachybotrys subsimplex* by G. R. Bisby (Trans. Br. Mycol. Soc. 26, 133-43 (1943)).

This *Stachybotrys subsimplex* strain G30-1140 is being stored at the Fermentation Research Institute, Agency of Industrial Science & Technology, Chiba City, Japan, as Deposit No. 4377.

Regarding the cultivation of the microorganism to be employed in the present invention, the general knowledge and techniques used in the culture of molds are applicable.

Namely, as the nutritional source medium, it is possible to employ the media which are used for the culture of ordinary molds. For example, various starches, starch hydrolyzates, corn meal, wheat flour, final molasses, etc., can be employed as carbon sources, while the nitrogen requirement can be supplied in the form of peptone, cottonseed oil dregs, meat extract, yeast extract, casein, corn steep liquor, malt extract, soybean dregs, skimmed milk, inorganic ammonium salts, inorganic nitrates, etc. As the inorganic salts, it is possible to employ calcium chloride, magnesium sulfate, phosphates, sodium chloride, potassium chloride, and so on. Furthermore, these carbon sources, nitrogen sources and inorganic salts can be used either singly or in appropriate combinations. In addition, when it is desired to promote the growth of the microorganism and bring about an increase in its enzyme production, it is possible to employ trace amounts of metallic salts, vitamins, amino acids, and so forth.

The culture conditions usually employed for molds are also applicable to the cultivation of this microorganism. Namely, in liquid culture, if this microbe is cultured for 7 to 14 days at pH 5 to 8 and 20° C. to 37° C. together with agitation to provide aeration, the enzyme of the present invention is accumulated in the culture fluid. In addition, if solid materials such as bran are employed, it is possible to carry out solid culture.

Next, an example will be presented of a method whereby the new neutral glucoamylase which is the objective of the present invention can be recovered from the cultured material. In the case of liquid culture, the mycelia are eliminated by any of the publicly-known methods; then the filtrate can be concentrated under reduced pressure, or the enzyme can be salted out with the other proteins by adding inorganic salts such as ammonium sulfate to the filtrate, or the enzyme can be precipitated out and concentrated by the addition of an organic solvent such as acetone or isopropanol.

In the case of solid culture, the enzyme is first extracted from the cultured material by the use of water or a buffer solution. Then, as in the case of liquid culture, it is possible to obtain the enzyme in a concentrated form.

The crude preparations of this new neutral enzyme obtained in this way can then be purified by carrying out the previously-mentioned purification techniques.

It is possible to employ this new neutral glucoamylase of the present invention for the saccharification of liquefied starch when producing dextrose from starch. Especially, if the present enzyme is used and the saccharification is carried out at pH 6.0 to 6.5, there is, as was mentioned earlier, little reverse reaction occurrence, and this results in an increased yield of dextrose being obtainable in comparison with the cases of employing the conventional glucoamylases and carrying out the saccharification under acidic conditions.

The invention is further illustrated by reference to the following examples in which all parts and percentages are by weight unless otherwise noted.

EXAMPLE 1

A liquid culture medium containing 5% soluble starch, 2% corn steep liquor, 0.5% cottonseed oil dregs, 0.5% yeast extract, 0.1% dipotassium phosphate, 0.05% magnesium sulfate and 0.01% calcuim chloride was adjusted to pH 7.0 and 100 ml of this was placed in a 500-ml Erlenmeyer flask. This medium was sterilized at 121° C. for 10 minutes, inoculated with *Stachybotrys subsimplex* strain G30-1140, and incubated at 30° C. for 7 days on a shaker. After the culture was completed, the mycelia were eliminated from the culture fluid by filtration. The filtrate was found to contain 70 units of glucoamylase activity per milliliter.

This filtrate was next frozen for one night at −20° C. and then thawed at room temperature. The insoluble matter was removed by centrifugation. Two volumes of cold isopropanol was then added to this solution and it was left standing at 4° C. for one night so that the enzyme would be precipitated out. The supernatant was removed by decantation and the precipitate was dissolved in a 0.05 M tris-HCl buffer solution containing 1 mM EDTA and having a pH of 7.5. This enzyme-containing solution was then dialyzed against the same buffer at 4° C. for one night. DEAE-cellulose which had been equilibrated with the same buffer solution was then added to the dialyzed enzyme solution and the enzyme was adsorbed to this carrier. After washing this DEAE-cellulose with the same buffer, the enzyme was eluted from it using a solution of the same buffer containing NaCl at a concentration of 0.3 M. Next, two volumes of cold isopropanol was added to the eluate to cause the enzyme to precipitate, and the precipitate was collected by centrifugation. This precipitate was then dissolved in the 0.05 M tris-HCl buffer (pH 7.5) containing 1 mM EDTA, followed by overnight dialysis against the same buffer solution. The dialyzed enzyme solution was next applied to a column of DEAE-cellulose which had been equilibrated with the same 0.05 M tris-HCl buffer (pH 7.5) containing 1 mM EDTA. Elution of the enzyme from this column was carried out by linearly increasing the concentration of NaCl in the same buffer solution up to 0.5 M. The fractions of the eluate which contained the enzyme were then pooled and two volumes of cold isopropanol was added in order to precipitate the enzyme out of this solution and concentrate it. The concentrated enzyme was next applied to a column of Sephadex G-150 which had been equilibrated with a 0.05 M tris-HCl buffer solution (pH 7.0) containing 1 mM EDTA, and elution was carried out using the same buffer. The eluted fractions which showed enzyme activity were then pooled, and two volumes of cold isopropanol was added to this to precipitate out the enzyme. This resulted in the recovery of the enzyme in a purified and concentrated form. The specific activity of this purified enzyme was found to be 127 units per milligram of protein.

EXAMPLE 2

To a 30% solution of a spray-dried maltodextrin (D.E. about 10) in 0.05 M acetate buffer at pH 6.5 was added the purified glucoamylase of Example 1. The enzyme was added at a dosage of 0.20 units of enzyme per gram of substrate on a dry solids basis. After the solution had been incubated at 55° C. for 72 hours, the dextrose content of the filtered hydrolyzate, as determined by high performance liquid chromatography, was 96.5% of the total carbohydrate.

EXAMPLE 3

Starch was converted to a 10.2 D.E. starch hydrolyzate using bacterial alpha-amylase from *B. licheniformis* according to the general procedure given in U.S. Pat. No. 3,912,590. The solution was boiled for 5 minutes after adjusting the pH to 2.0 with 2 N HCl to inactivate the residual alpha-amylase. The starch hydrolyzate solution was then adjusted to pH 6.2 and diluted to the desired concentration before treatment with 0.20 units of the purified glucoamylase of Example 1 per gram of substrate (dry solids basis). The solution was incubated at 55° C. in a stoppered tube. The pH was adjusted to 6.2 after 5 hours and 48 hours. After the solution had been incubated for 72 hours, the dextrose content of the filtered hydrolyzate, as determined by high performance liquid chromatography, was 97.6% of the total carbohydrate. The final concentration of the solution was 31.2% on a dry solids basis.

When saccharification tests at the same substrate concentration were carried out with commercial glucoamylase from *A. niger* under its optimum conditions (pH 4.3 at 60° C.), the corresponding dextrose yield was 96.5%. Similarly, the glucoamylase from *R. niveus* at pH 5.0 and 55° C. gave a dextrose yield of 97%. Dextrose yields were about 1% lower when the saccharification tests were carried out with the commercial glucoamylases under the conditions used for the new enzyme. These results show that the new glucoamylase of this invention gives higher yields of dextrose than do the commercial glucoamylases even when each enzyme is utilized under its optimum reaction conditions.

We claim:

1. A glucoamylase enzyme preparation characterized in that it has a molecular weight of about 50,000 as determined by Sephadex G-150 column chromatography, an optimum glucoamylase activity in the range of about pH 6.0 to 6.5 at 60° C. and that it has maximum glucoamylase activity at about 65° C. as measured by a 10-minute reaction on a 2% maltodextrin solution at pH 6.0.

2. The enzyme preparation of claim 1 further characterized in that it is obtained from a strain of the fungus *Stachybotrys subsimplex*.

3. The enzyme preparation of claim 2 further characterized in that it is obtained from the strain of *Stachybotrys subsimplex*, Fermentation Research Institute, Deposit No. 4377.

4. A process for producing a glucoamylase enzyme preparation which comprises culturing cells of a strain of *Stachybotrys subsimplex* in a nutrient medium and isolating the glucoamylase enzyme preparation from the culture medium.

5. The process of claim 4, wherein the strain of *Stachybotrys subsimplex* is Fermentation Research Institute Deposit No. 4377.

6. A glucoamylase prepared according to claim 4, which has a molecular weight of about 50,000 as determined by Sephadex G-150 column chromatography and an optimum glucoamylase activity in the range of about pH 6.0 to 6.5.

7. A glucoamylase prepared according to claim 4, which has a molecular weight of about 50,000 as determined by Sephadex G-150 column chromatography and a maximum glucoamylase activity at about 65° C. as measured by a 10-minute reaction on a 2% maltodextrin solution at pH 6.0.

8. A glucoamylase prepared according to claim 4, which is capable of converting a 30% by weight solution of a 10 D.E. starch hydrolyzate to a product containing at least about 96% dextrose on a dry solids basis when reacted with the starch hydrolyzate at pH 6.0 to 6.5 at 55° C.

9. In a process for producing a syrup of high dextrose content by saccharifying a liquefied starch to dextrose, the improvement which comprises saccharifying the liquefied starch at pH between 6.0 and 6.5 in the presence of a glucoamylase which has a molecular weight of about 50,000 as determined by Sephadex G-150 column chromatography obtained from the genus Stachybotrys thereby obtaining improved yields of dextrose.

10. The process of claim 9, wherein the glucoamylase is obtained from the strain of *Stachybotrys subsimplex*, Fermentation Research Institute Deposit No. 4377.

11. The process of claim 10, wherein the saccharification is carried out at a temperature of from about 50° C. to about 65° C.

* * * * *

UNITED STATES PATENT AND TRADEMARK OFFICE
CERTIFICATE OF CORRECTION

PATENT NO. : 4,254,225
DATED : March 3, 1981
INVENTOR(S) : Masaki Tamura, Mizuho Shimizu, Minoru Tago It is certified that error appears in the above-identified patent and that said Letters Patent are hereby corrected as shown below:

Fig. 1, Title, change "TEMPERATURE" to read --pH--.

Fig. 4, Abscissa, "Treatmen" should read --Treatment--.

Column 3, line 6, delete "B6.5" and insert --6.5--.

Column 3, line 51, "glycoamylase" should read --glucoamylase--.

Column 5, line 31, "isloated" should read --isolated--.

Signed and Sealed this

Twenty-second Day of September 1981

[SEAL]

Attest:

GERALD J. MOSSINGHOFF

Attesting Officer

Commissioner of Patents and Trademarks